United States Patent
Harada et al.

(10) Patent No.: US 9,060,942 B2
(45) Date of Patent: Jun. 23, 2015

(54) OIL-IN-WATER EMULSION SUNSCREEN COSMETIC COMPOSITION

(71) Applicants: Taichi Harada, Yokohama (JP); Kahori Ishida, Yokohama (JP); Kazuhiro Yamaguchi, Yokohama (JP)

(72) Inventors: Taichi Harada, Yokohama (JP); Kahori Ishida, Yokohama (JP); Kazuhiro Yamaguchi, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 87 days.

(21) Appl. No.: 13/947,455

(22) Filed: Jul. 22, 2013

(65) Prior Publication Data

US 2014/0030298 A1  Jan. 30, 2014

(30) Foreign Application Priority Data

Jul. 24, 2012 (JP) ................. 2012-164180

(51) Int. Cl.
| | |
|---|---|
| A61Q 17/04 | (2006.01) |
| A61K 8/27 | (2006.01) |
| A61K 8/36 | (2006.01) |
| A61K 8/37 | (2006.01) |
| A61K 8/41 | (2006.01) |
| A61K 8/49 | (2006.01) |
| A61K 8/02 | (2006.01) |
| A61K 8/06 | (2006.01) |

(52) U.S. Cl.
CPC . *A61K 8/27* (2013.01); *A61Q 17/04* (2013.01); *A61K 8/361* (2013.01); *A61K 8/37* (2013.01); *A61K 8/416* (2013.01); *A61K 8/4966* (2013.01); *A61K 8/0241* (2013.01); *A61K 8/062* (2013.01); *A61K 2800/413* (2013.01); *A61K 2800/623* (2013.01)

(58) Field of Classification Search
None
See application file for complete search history.

(56) References Cited

U.S. PATENT DOCUMENTS

2010/0247458 A1* 9/2010 Kakoki et al. .................. 424/59
2012/0269747 A1* 10/2012 Iimura et al. .................... 424/59

FOREIGN PATENT DOCUMENTS

| JP | 2009-84171 | 4/2009 |
| JP | 2012-111726 | 6/2012 |
| JP | 2012111726 A * | 6/2012 |

* cited by examiner

*Primary Examiner* — H. Sarah Park
(74) *Attorney, Agent, or Firm* — Andrew F. Young, Esq.; Lackenbach Siegel, LLP

(57) ABSTRACT

Provided is an oil-in-water emulsion sunscreen cosmetic composition that can provide high protection ability against UVA and excellent emulsion stability. The oil-in-water emulsion sunscreen cosmetic composition is characterized in that it contains (A) a hydrophobized zinc oxide having an absorbance of 0.3 or more at a wavelength of 370 nm, (B) a UVA absorber being solid at room temperature, (C) a UVB absorber, (D) a liquid-state higher fatty acid, (E) a nonionic surfactant, (F) a volatile oil, (G) a quaternary ammonium compound having a long-chain aliphatic group and (H) water. Particularly, it is preferable that the hydrophobized zinc oxide has an average particle size within a range of 35 to 100 nm; the hydrophobized zinc oxide is hydrophobidized by use of hydrogen dimethicone; the quaternary ammonium compound having a long-chain aliphatic group is distearyldimethylammonium chloride; and the UVB absorber is octylmethoxy cinnamate.

12 Claims, No Drawings

OIL-IN-WATER EMULSION SUNSCREEN COSMETIC COMPOSITION

CROSS REFERENCE TO RELATED APPLICATIONS

This application claims priority from JP 2012-164180 filed Jul. 24, 2012, the entire contents of which is incorporated herein by reference.

FIGURE SELECTED FOR PUBLICATION

None

BACKGROUND OF THE INVENTION

1. Field of the Invention

The present invention relates to an oil-in-water emulsion sunscreen cosmetic composition. More specifically, the present invention relates to an oil-in-water emulsion sunscreen cosmetic composition having high protection ability against UVA and excellent emulsion stability, which are achieved by adding a hydrophobized zinc oxide satisfying certain physical conditions as an ultraviolet scattering agent as well as a quaternary ammonium compound having a long-chain aliphatic group as an emulsion stabilizer.

2. Description of the Related Art

An oil-in-water emulsion sunscreen cosmetic having a hydrophobized ultraviolet scattering agent dispersed in an internal phase is useful as a formulation system which can provide not only a fresh sense of use but also high protection against UV rays. As an ultraviolet scattering agent, titanium oxide and zinc oxide are mainly employed. However, whiteness and squeaky feeling of titanium oxide stand out in comparison with zinc oxide. Thus, in order to prepare an oil-in-water emulsion sunscreen cosmetic composition having excellent appearance and a sense of use, it is desirable to use zinc oxide. However, it is difficult to stably disperse zinc oxide in an oil-in-water emulsion composition. In addition, if a large amount of zinc oxide is added, an application surface looks excessively white and powdery, with the result that satisfactory end result and texture tend not to be obtained.

To overcome such problems on dispersibility of zinc oxide, the following methods have so far been proposed. JP-A 2009-084171, the entire contents of which are incorporated herein by reference, proposes a method of enhancing dispersibility of zinc oxide by treating the surface of zinc oxide fine particles with a silicone compound having a specific structure and using volatile organopolysiloxane in combination with a silicone dispersant. JP-A 2012-111726, the entire contents of which are incorporated herein by reference, proposes a method of improving dispersion stability of zinc oxide in an oil-in-water emulsion composition by hydrophobizing zinc oxide fine powder with octyltriethoxysilane and/or dimethylpolysiloxane and using a certain silicone or sugar ester in combination.

The stability of zinc oxide is relatively satisfactory if the particle size of zinc oxide is several nm or less; however, particularly, it is difficult to stably disperse a zinc oxide powder having a particle size larger than this in an oil-in-water emulsion composition. Thus, improvement is still desired.

SUMMARY OF THE INVENTION

The present invention is made in consideration of the aforementioned problems and directed to provide an oil-in-water emulsion sunscreen cosmetic composition that provides high protection ability against UVA and excellent emulsion stability.

The present inventors made intensive studies with a view to solving the aforementioned problems. As a result, they found that high protection ability against OVA and excellent emulsion stability can be achieved by adding hydrophobized zinc oxide satisfying certain conditions as an ultraviolet scattering agent as well as a quaternary ammonium compound having a long-chain aliphatic group as a dispersant. Based on the finding, the present invention was accomplished.

More specifically, the present invention provides an oil-in-water emulsion sunscreen cosmetic composition containing the following components (A) to (H):

(A) a hydrophobized zinc oxide having an absorbance of 0.3 or more at a wavelength of 370 nm,
(B) a UVA absorber being solid at room temperature,
(C) a UVB absorber,
(D) a liquid-state higher fatty acid,
(E) a nonionic surfactant,
(F) a volatile oil,
(G) a quaternary ammonium compound having a long-chain aliphatic group, and
(H) water.

A hydrophobized zinc oxide has been widely used as an ultraviolet scattering agent to be added to an oil-in-water emulsion sunscreen cosmetic composition. Of the hydrophobized zinc oxides, especially, a hydrophobized zinc oxide having an absorbance of 0.3 or more at a wavelength of 370 nm was found to provide particularly high protection ability against OVA. Such a hydrophobized zinc oxide capable of providing high protection ability against OVA can exert sufficient sunscreen effect even in a low content, and thus, a problem of stability depending upon the content can be overcome.

Furthermore, it was found that the stability of an emulsion cosmetic composition containing a hydrophobized zinc oxide can be significantly improved by adding a quaternary ammonium compound having a long-chain aliphatic group as a dispersant.

The oil-in-water emulsion sunscreen cosmetic composition of the present invention can attain excellent protection ability against UVA since a hydrophobized zinc oxide providing high protection ability against UVA is employed, as well as can suppress powdery and sticky feeling of a final product since the requisite content of hydrophobized zinc oxide can be reduced. In addition, the dispersion stability of the hydrophobized zinc oxide can be improved by adding a quaternary ammonium compound having a long-chain aliphatic group. Because of this, even if the cosmetic composition has high protection ability against UVA, excellent emulsion stability can be achieved.

DETAILED DESCRIPTION OF THE PREFERRED EMBODIMENTS

Now, the present invention will be more specifically described below.

<(A) Hydrophobized Zinc Oxide>

The hydrophobized zinc oxide to be used in the present invention has an absorbance of 0.3 or more, more preferably 0.4 or more, further preferably 0.5 or more, still further preferably 0.6 or more at a wavelength of 370 nm. Although the upper limit of the absorbance should not specifically be restricted, it may generally be, for example, 0.8, 0.85, 0.9, or 0.95. If the absorbance at a wavelength of 370 nm is less than 0.3, it is difficult to obtain high protection ability against UVA. If the content of a hydrophobized zinc oxide having an absorbance of less than 0.3 increases in order to obtain sufficient UVA protection, the resultant oil-in-water emulsion cosmetic composition may become instable and sticky.

In the present invention, the absorbance of a hydrophobized zinc oxide can be determined by dispersing 10% by mass of a hydrophobized zinc oxide in a solution mixture containing 99% dimethicone (KF-96-1000cs manufactured by Shin-Etsu Chemical Co., Ltd.) and 1% PEG-10 dimethicone (KF-6017P manufactured by Shin-Etsu Chemical Co., Ltd.), applying the dispersion solution onto a quartz plate so as to obtain a thickness of 10 µm and measuring absorbance by a general absorptiometer at a wavelength of 370 nm. At this time, a solution mixture containing 99% dimethicone (KF-96-1000cs manufactured by Shin-Etsu Chemical Co., Ltd.) and 1% PEG-10 dimethicone (KF-6017P manufactured by Shin-Etsu Chemical Co., Ltd.) without the hydrophobized zinc oxide is used as a blank.

A hydrophobized zinc oxide preferably has an average particle size (which refers to a particle size corresponding to 50% in mass in the particle size distribution by laser diffraction measurement) of 35 to 100 nm, further preferably 40 to 80 nm, and most preferably 50 to 80 nm. By making an average particle size within the range, the absorbance of the hydrophobized zinc oxide becomes 0.3 or more at a wavelength of 370 nm. If the average particle size is less than 35 nm, high protection ability against UVA may not be obtained. If the average particle size exceeds 100 nm, makeup with the cosmetic composition tends to show up too white.

The hydrophobized zinc oxide of the present invention can be also defined as zinc oxide making a critical wavelength of the composition containing the zinc oxide to 370 nm or more (the critical wavelength is defined in the final rule published in June, 2011 (Federal Register, Vol. 76, No. 117, pages 35620-35665, Jun. 17, 2011) by FDA (U.S. Food and Drug Administration)).

The critical wavelength refers to a reference indicating the broad protection ability defined in consideration of the balance between the protective activities against medium-wavelength ultraviolet rays (UVB: wavelength of 290 to 320 nm) and long-wavelength UV rays (UVA: wavelength of 320 to 400 nm) in response to demands that skin should be protected not only from UVB, which are known to cause e.g., sun burn and inflammation, but also from UVA, which is a possible cause of e.g., photoaging.

The critical wavelength ($\lambda c$) is a value defined by the following formula.

$$\int_{290}^{\lambda c} A(\lambda)d\lambda = 0.9 \int_{290}^{400} A(\lambda)d\lambda$$ [Numerical Expression 1]

To describe in brief, a UV protective cosmetic composition is applied to a certain plate and irradiated with 4MED light, and then an absorption spectrum is measured. Based on 100% of the integral value of absorbance at 290 nm to 400 nm in the absorption spectrum, the wavelength providing an integrated value of 90% when absorbance is integrated from 290 nm at intervals of 1 nm is defined as the critical wavelength ($\lambda c$).

The hydrophobized zinc oxide to be used in the present invention can be obtained by hydrophobizing zinc oxide by a method known in the art. Examples of the hydrophobizing method include, but not particularly limited to, treatment with silicone such as methylhydrogenpolysiloxane and methylpolysiloxane; treatment with fluorine such as perfluoroalkyl phosphate and perfluoro alcohol; treatment with an amino acid such as N-acyl glutamine acid; other treatments including treatment with lecithin; treatment with metal soap; treatment with a fatty acid; and treatment with an alkyl phosphate. Of them, zinc oxide a surface of which is treated with silicone is preferably used.

Examples of the silicone to be used for surface treatment include, but not particularly limited to, various types of silicone oils such as methylpolysiloxane, methylphenylpolysiloxane, methylhydrogenpolysiloxane, methylcyclopolysiloxane, octamethylcyclotetrasiloxane, decamethylcyclopentasiloxane, dodecamethylcyclohexasiloxane, octamethyltrisiloxane, tetradecamethylhexasiloxane, a dimethylsiloxane-methylhydrogensiloxane copolymer, a dimethyl siloxane-methyl(polyoxyethylene)siloxane-methyl(polyoxypropylene)siloxane copolymer, a dimethylsiloxane-methyl(polyoxyethylene)siloxane copolymer, a dimethylsiloxane-methyl(polyoxypropylene)siloxane copolymer, a dimethylsiloxane-methylcetyloxysiloxane copolymer and a dimethylsiloxane-methylstearoxysiloxane copolymer. Of them, hydrogen dimethicone (dimethylsiloxane-methylhydrogensiloxane copolymer) is preferably used for surface treatment in the present invention.

The amount of silicone to be used for surface treatment of zinc oxide is usually about 1 to 20% by mass, preferably 2 to 14% by mass, more preferably 2 to 10% by mass, and particularly 2 to 5% by mass with respect to the surface-treated zinc oxide (100% by mass).

The hydrophobized zinc oxide to be used in the present invention may be a commercially available product. Specific examples thereof include, but not limited to, MZY-203S (treated with hydrogen dimethicone, average particle size: 50 nm, absorbance at a wavelength of 370 nm=0.628, manufactured by Tayca Corp.) and MZY-153S (treated with hydrogen dimethicone, average particle size: 80 nm, absorbance at a wavelength of 370 nm=0.445, manufactured by Tayca Corp.).

The content of the hydrophobized zinc oxide fall within the range of preferably 3 to 35% by mass, further preferably 5 to 30% by mass, and most preferably 8 to 20% by mass relative to the total amount of oil-in-water emulsion sunscreen cosmetic composition. If the content is less than 3% by mass relative to the cosmetic composition, sufficient protective activity against UVA tends not to be obtained. In contrast, if the content exceeds 35% by mass, sense of use tends to deteriorate in view of e.g., sticky feeling and dispersion stability and makeup in view of transparency and others tend to deteriorate.

<(B) UVA Absorber>

The UVA absorber to be used in the present invention is a solid substance at room temperature (about 25° C.) Excellent emulsion stability and high protective activity against UVA can be achieved by addition of the UVA absorber as a solid substance at room temperature.

Examples of the UVA absorber commercially available include bisethylhexyloxyphenolmethoxyphenyltriazine {trade name: Tinosorb S (BASF)}, diethylamino hydroxybenzoyl hexyl benzoate {trade name: Uvinul A Plus (BASF)} and t-butyl methoxydibenzoylmethane {trade name: Parsol 1789 (DSM Nutrition Japan K.K.)}. These may be used alone or in appropriate combination with two types or more.

The content of a UVA absorber falls within the range of preferably 0.1 to 10% by mass, further preferably 1 to 8% by mass, and most preferably 1.5 to 5% by mass relative to the total amount of an oil-in-water emulsion sunscreen cosmetic composition. If the content of a UVA absorber is less than 0.1% by mass, sufficient protective activity against UVA may not be obtained. In contrast, if the content exceeds 10% by mass, the UVA absorber may precipitate with the passage of time.

<(C) UVB Absorber>

The UVB absorber to be used in the present invention is not particularly limited as long as it is generally used in cosmetics for skin. Examples thereof include 2-ethylhexyl paramethoxycinnamate (octyl methoxy cinnamate), isopropyl methoxy cinnamate, para-aminobenzoic acid (hereinafter, simply referred to as "PABA"), ethyl PABA, ethyl-dihydroxypropyl PABA, ethylhexyl-dimethyl PABA, homosalate, ethylhexyl salicylate, 3-benzylidene camphor, 4-methylbenzylidene camphor, benzylidene camphor sulfonic acid, camphor benzalkonium methosulfate, polyacrylamide methylbenzylidene camphor, diethylhexyl butamidotriazone, 2,4,6-tris[4-(2-ethylhexyloxycarbonyl)anilino]-1,3,5-triazine, disodium phenyldibenzimidazole tetrasulfonate, polyorganosiloxane having a benzalmalonate functional group and octocrylene. These may be used alone or in appropriate combination of two types or more.

Among them, particularly preferable UVB absorber is octylmethoxy cinnamate (2-ethylhexyl paramethoxycinnamate) and commercially available one under a trade name of, e.g., "Parsol MCX" (DSM Nutrition Japan K.K.) can be used.

The content of a UVB absorber falls within the range of preferably 0.1 to 15% by mass, further preferably 1 to 10% by mass, and most preferably 1.5 to 7.5% by mass relative to the total amount of an oil-in-water emulsion sunscreen cosmetic composition. If the content of a UVB absorber is less than 0.1% by mass, protection ability against UVB region becomes insufficient, with the result that wide-range ultraviolet absorption ability may not be obtained. In contrast, if the content exceeds 15% by mass, sense of use (sticky) and stability tends to deteriorate.

<(D) Liquid-State Higher Fatty Acid>

As the liquid-state higher fatty acid to be used in the present invention, for example, isostearic acid, oleic acid, linoleic acid and linolenic acid are mentioned, and particularly isostearic acid is preferably used.

In the present invention, a liquid-state higher fatty acid is a component constituting an oil content of the internal phase of an oil-in-water emulsion sunscreen cosmetic, in combination with (F) a volatile oil content (described later). The aforementioned (A) hydrophobized zinc oxide is homogeneously dispersed in the oil content in the internal phase in the present invention; however, the dispersibility reduces if the liquid-state higher fatty acid is not added.

The content of a liquid-state higher fatty acid is preferably 0.1 to 2% by mass, further preferably 0.3 to 1.8% by mass, and most preferably 0.5 to 1.5% by mass relative to the total amount of oil-in-water emulsion sunscreen cosmetic composition. If the content of a liquid-state higher fatty acid is less than 0.1% by mass, the dispersibility of the hydrophobized zinc oxide may reduce. In contrast, if the content exceeds 2% by mass, sense of use (sticky) and stability tend to deteriorate.

<(E) Nonionic Surfactant>

The nonionic surfactant to be used in the present invention is a component to be added as an emulsifier in order to produce a stable oil-in-water emulsion composition in the present invention.

Specific examples of lipophilic nonionic surfactants include sorbitan fatty acid esters (e.g., sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, diglycerol sorbitan tetra-2-ethylhexylate); glycerin polyglycerin fatty acids (e.g., mono cotton seed oil fatty acid glycerin, glyceryl monoerucate, glycerin sesquioleate, glyceryl monostearate, α,α'-glycerin oleate pyroglutamate, monostearate glycerin malic acid); propylene glycol fatty acid esters (e.g., propylene glycol monostearate); hydrogenated castor oil derivatives; and glycerin alkylether.

Furthermore, examples of hydrophilic nonionic surfactants include POE-sorbitan fatty acid esters (e.g., POE-sorbitan monooleate, POE-sorbitan monostearate, POE-sorbitan tetraoleate); POE sorbit fatty acid esters (e.g., POE-sorbit monolaurate, POE-sorbit monooleate, POE-sorbit pentaoleate, POE-sorbit monostearate); POE-glycerin fatty acid esters (e.g., POE-monooleates such as POE-glycerin monostearate, POE-glycerin monoisostearate and POE-glycerin triisostearate); POE-fatty acid esters (e.g., POE-distearate, POE-monodioleate, ethylene glycol distearate); POE-alkylethers (e.g., POE-lauryl ether, POE-oleyl ether, POE-stearyl ether, POE-behenyl ether, POE-2-octyl dodecyl ether, POE-cholestanol ether); pluronics (e.g., pluronic); POE•POP-alkyl ethers (e.g., POE•POP-cetyl ether, POE•POP-2-decyltetradecyl ether, POE•POP-monobutyl ether, POE•POP-hydrogenated lanolin, POE•POP-glyceryl ether); tetra POE•tetra POP-ethylene diamine condensates (e.g., Tetronic); POE-castor oil•POE-hydrogenated castor oil derivatives (e.g., POE-castor oil, POE-hydrogenated castor oil, POE-hydrogenated castor oil monoisostearate, POE-hydrogenated castor oil triisostearate, POE-hydrogenated castor oil monopyroglutamic monoisostearic diester, POE-hydrogenated castor oil maleic acid); POE-beeswax•lanolin derivatives (e.g., POE-sorbitol beeswax); alkanol amides (e.g., palm oil fatty acid diethanol amide, laurate monoethanol amide, fatty acid isopropanol amide); POE-propylene glycol fatty acid esters; POE-alkylamines; POE-fatty acid amides; sucrose fatty acid esters; alkylethoxydimethylamine oxides; and trioleyl phosphoric acid.

In the present invention, a hydrophilic surfactant is preferably used.

The content of a nonionic surfactant is preferably 0.2 to 3% by mass relative to the total amount of an oil-in-water emulsion sunscreen cosmetic, further preferably 0.3 to 2% by mass, and most preferably 0.5 to 1.5% by mass.

If the content of a nonionic surfactant is outside the above range, the stability of the oil-in-water emulsion cosmetic may decrease.

<(F) Volatile Oil>

As the volatile oil to be used in the present invention, for example, a relatively low molecular-weight hydrocarbon oil, a relatively low molecular-weight linear silicone and a relatively low molecular-weight cyclic silicone are mentioned, and particularly, light liquid isoparaffin, isododecane, isohexadecane, volatile dimethylpolysiloxane or cyclic polysiloxane is preferable. Specifically, octamethylcyclotetra siloxane, decamethylcyclopenta siloxane, dodecamethylcyclohexasiloxane and hexadecamethylcycloheptasiloxane are preferable; and particularly preferably, light liquid isoparaffin, isododecane, isohexadecane and decamethylcyclopentasiloxane are mentioned.

The volatile oil to be used in the present invention is a component constituting the internal oil phase of an oil-in-water emulsion sunscreen cosmetic composition, in combination with (D) a liquid-state higher fatty acid. (A) a hydrophobized zinc oxide as mentioned above is homogeneously dispersed in the internal phase.

The content of the volatile oil is preferably 5 to 30% by mass, further preferably 7 to 20% by mass, and most preferably 10 to 20% by mass relative to the total amount of an oil-in-water emulsion sunscreen cosmetic composition. If the content of the volatile oil is outside the above range, the dispersibility of hydrophobized zinc oxide may deteriorate and fresh sense of use may reduce.

<(G) Quaternary Ammonium Compound having a Long-Chain Aliphatic Group>

The quaternary ammonium compound having a long-chain aliphatic group to be used in the present invention is added in order to stably disperse hydrophobized zinc oxide in an oil-in-water emulsion sunscreen cosmetic. Such a quaternary ammonium compound is excellent in stably dispersing a zinc oxide powder of a relatively large particle size in an oil-in-water emulsion composition, compared to other dispersants generally used.

As the quaternary ammonium compound having a long-chain aliphatic group, specifically, a quaternary ammonium chloride, for example, an alkyltrimethylammonium chloride having an alkyl group of about 8 to 22 carbon atoms is mentioned. Examples thereof include octyltrimethylammonium chloride, dodecyltrimethylammonium chloride, stearyltrimethylammonium chloride, behenyltrimethylammonium chloride, cetyltrimethylammonium chloride, didodecyldimethylammonium chloride, dioctadecyldimethylammonium chloride and distearyldimethylammonium chloride.

The content of a quaternary ammonium compound having a long-chain aliphatic group is preferably 0.08 to 0.8% by mass relative to the total amount of an oil-in-water emulsion sunscreen cosmetic, and further preferably 0.1 to 0.8% by mass. If the content is outside the above range, hydrophobized zinc oxide may not be stably dispersed.

<(H) Water>

Water to be used in the present invention is not particularly limited. More specifically, purified water and ion exchange water are mentioned. Water is a component constituting the external phase, i.e., the water phase of an oil-in-water emulsion sunscreen cosmetic, in combination with other aqueous components.

The water content is appropriately determined depending upon the content of an oil content constituting the internal oil phase and preferably 35 to 65% by mass, further preferably 40 to 60% by mass, and most preferably 40 to 50% by mass relative to the total amount of an oil-in-water emulsion sunscreen cosmetic composition. If the water content is outside the above range, the stability of the oil-in-water emulsion cosmetic composition may decrease and fresh sense of use may reduce.

The oil-in-water emulsion sunscreen cosmetic composition of the present invention may contain, other than the aforementioned essential components, components generally added to cosmetics, such as a humectant, a thickening agent, a powder, an alcohol, a natural polymer, a synthetic polymer, a saccharide, an antioxidant, a buffer, any kind of extract, a stabilizer, a preservative, a dye and a fragrance, as long as they do not undermine the effect of the invention.

A method for producing the oil-in-water emulsion sunscreen cosmetic composition of the present invention is not particularly limited. The sunscreen cosmetic composition may be prepared, for example, by adding (A) a hydrophobized zinc oxide, (B) and (C) UV ray absorbers, (D) a liquid-state higher fatty acid, (E) a lipophilic nonionic surfactant, (F) a volatile oil, (G) a quaternary ammonium compound having a long-chain aliphatic group, and other oil contents and lipophilic components and stirring the mixture to prepare an oil phase on the one hand, adding (H) water, (E) a hydrophilic nonionic surfactant and other aqueous components and stirring the mixture to prepare a water phase on the other hand, and finally emulsifying the water phase and the oil phase in accordance with a conventional method.

The oil-in-water emulsion sunscreen cosmetic composition of the present invention can provide high protection ability against UVA and excellent emulsion stability by using a hydrophobized zinc oxide satisfying certain conditions and a quaternary ammonium compound having a long-chain aliphatic group, in combination. Because of this, the sunscreen cosmetic can be suitably used, for example, as a sunscreen milky lotion and a sunscreen cream.

The oil-in-water emulsion sunscreen cosmetic composition of the present invention has a critical wavelength ($\lambda c$) as defined above of 370 nm or higher, preferably 375 nm or higher, further preferably 380 nm or higher. Accordingly, the oil-in-water emulsion sunscreen cosmetic composition of the present invention can effectively protect wide-range UV radiation from UVA to UVB.

EXAMPLES

Now, the present invention will be more specifically described by way of Examples, below; however, the present invention is not limited by these. Note that, unless otherwise specified, the content is expressed by % by mass relative to the total amount.

A milky lotion as an oil-in-water emulsion sunscreen cosmetic composition was prepared in accordance with each of the formulations shown in Table 1 by a conventional method and evaluated as follows.

<Emulsion Stability of Oil-in-Water Emulsion Cosmetic>

Milky lotions of Examples and Comparative Example were allowed to stand still at thermostatic chambers of $-5°$ C., $0°$ C., RT, $37°$ C. and $50°$ C. for a month. Thereafter, the dispersion state of emulsion particles in each of the milky lotions was visually observed by an optical microscope (400×) and evaluated based on the following evaluation criteria.

<Evaluation Criteria>

◯: Emulsion particles are homogeneously dispersed and no appearance change is observed in milky lotions allowed to stand still in thermostatic chambers placed at any one of the temperatures, x: Emulsion particles are not homogeneously dispersed and appearance change is observed in milky lotions allowed to stand still in thermostatic chamber placed at least one of the temperatures.

<Protection Ability Against UVA>

Each of the milky lotions according to Examples and Comparative Examples was applied onto a PMMA plate so as to be at 0.75 mg/cm$^2$ and absorbance was measured by an absorptiometer (name of apparatus: "U-4100 type spectrophotometer" (manufactured by Hitachi High-Technologies Corporation)) at a wavelength of 370 nm. An uncoated PMMA plate was used as a blank.

TABLE 1

| Name of materials | Example 1 | Comparative Example 1 | Comparative Example 2 | Comparative Example 3 | Comparative Example 4 | Comparative Example 5 | Comparative Example 6 | Comparative Example 7 | Example 2 | Example 3 | Example 4 | Comparative Example 8 |
|---|---|---|---|---|---|---|---|---|---|---|---|---|
| Water | Balance | Balance | Balance | Balance | Balance | Balance | Balance | Balance | Balance | Balance | Balance | Balance |
| Ethanol | 10 | 10 | 10 | 10 | 10 | 10 | 10 | 10 | 10 | 10 | 10 | 10 |
| Glycerin | 3 | 3 | 3 | 3 | 3 | 3 | 3 | 3 | 3 | 3 | 3 | 3 |
| Succinoglucan | 0.1 | 0.1 | 0.1 | 0.1 | 0.1 | 0.1 | 0.1 | 0.1 | 0.1 | 0.1 | 0.1 | 0.1 |
| (Dimethylacrylamide/sodium acryloyldimethyl taurate) cross polymer | 0.3 | 0.3 | 0.3 | 0.3 | 0.3 | 0.3 | 0.3 | 0.3 | 0.3 | 0.3 | 0.3 | 0.3 |
| Polyoxyethylene hydrogenated castor oil | 1 | 1 | 1 | 1 | 1 | 1 | 1 | 1 | 1 | 1 | 1 | 1 |
| Polypropylene glycol | 1 | 1 | 1 | 1 | 1 | 1 | 1 | 1 | 1 | 1 | 1 | 1 |
| Light isoparaffin | 18 | 18 | 18 | 18 | 18 | 18 | 18 | 18 | 18 | 18 | 18 | 18 |
| Isostearic acid | 0.8 | 0.8 | 0.8 | 0.8 | 0.8 | 0.8 | 0.8 | 0.8 | 0.8 | 0.8 | 0.8 | 0.8 |
| Sorbitan sesquiisostearate | | | 0.5 | | | | | | | | | |
| Bisbutyldimethicone polyglyceryl-3 | | | | 0.5 | | | | | | | | |
| Isostearyl alcohol | | | | | 0.5 | | | | | | | |
| PEG-10 dimethicone | | | | | | 0.5 | | | | | | |
| Polyglyceryl-2 diisostearate | | | | | | | 0.5 | | | | | |
| Distearyldimethylammonium chloride | 0.5 | | | | | | | 1 | 0.8 | 0.2 | 0.1 | 0.05 |
| Octylmethoxy cinnamate | 7.5 | 7.5 | 7.5 | 7.5 | 7.5 | 7.5 | 7.5 | 7.5 | 7.5 | 7.5 | 7.5 | 7.5 |
| Bisethylhexyloxyphenolmethoxyphenyl-triazine | 2.5 | 2.5 | 2.5 | 2.5 | 2.5 | 2.5 | 2.5 | 2.5 | 2.5 | 2.5 | 2.5 | 2.5 |
| Hydrophobized zinc oxide A*1 | 12 | — | — | — | — | — | — | — | — | — | — | — |
| Hydrophobized zinc oxide B*2 | — | 12 | 12 | 12 | 12 | 12 | 12 | 12 | 12 | 12 | 12 | 12 |
| Citric acid | Appropriate amount | Appropriate amount | Appropriate amount | Appropriate amount | Appropriate amount | Appropriate amount | Appropriate amount | Appropriate amount | Appropriate amount | Appropriate amount | Appropriate amount | Appropriate amount |
| Sodium citrate | Appropriate amount | Appropriate amount | Appropriate amount | Appropriate amount | Appropriate amount | Appropriate amount | Appropriate amount | Appropriate amount | Appropriate amount | Appropriate amount | Appropriate amount | Appropriate amount |
| Emulsion stability | ○ | ○ | X | X | X | X | X | X | ○ | ○ | ○ | X |
| Protection ability against UVA region (absorbance at 370 nm) | 0.57 | 0.49 | — | — | — | — | — | — | 0.56 | 0.53 | 0.60 | — |

*1 Octyltriethoxysilane-treated zinc oxide (average particle size = 20 nm, critical wavelength = 367 nm, absorbance at a wavelength of 370 nm = 0.236)
*2 Hydrogen dimethicone-treated zinc oxide (average particle size = 50 nm, critical wavelength = 376 nm, absorbance at a wavelength of 370 nm = 0.628, trade name "MZY-203S" (Tayca Corp.))

As is apparent from Table 1, the milky lotion of Example 1 containing hydrophobized zinc oxide 3 having an absorbance of 0.3 or more at a wavelength of 370 nm was excellent in UV protection ability against a UVA region compared to the milky lotion of Comparative Example 1 containing hydrophobized zinc oxide A having an absorbance of smaller than 0.3.

Furthermore, in Comparative Examples 2 to 6 in which distearyldimethylammonium chloride contained in Example 1 was replaced with another dispersant generally used in cosmetics, emulsion stability significantly decreased. Furthermore, if the content of distearyldimethylammonium chloride is excessively low, sufficient emulsion stability was not obtained (Comparative Example 8); however, even if the content is excessively large, emulsion stability decreased as a result (Comparative Example 7).

Formulation examples of the oil-in-water emulsion sunscreen cosmetic composition of the present invention will be shown below. The present invention is not limited by the formulation examples, needless to say, is specified by the claims. Note that, all the contents are expressed by % by mass relative to the total amount.

Formulation Example 1

Milky Lotion

| (Name of component) | Content (%) |
| --- | --- |
| (1) Water | Balance |
| (2) Ethanol | 10 |
| (3) Glycerin | 3 |
| (4) Succinoglucan | 0.1 |
| (5) (Dimethylacrylamide/sodium acryloyldimethyl taurate) cross polymer | 0.3 |
| (6) Polyoxyethylene hydrogenated castor oil | 1 |
| (7) Polypropylene glycol | 1 |
| (8) Light isoparaffin | 18 |
| (9) Isostearic acid | 0.8 |
| (10) Distearyldimethylammonium chloride | 0.5 |
| (11) Octylmethoxy cinnamate | 7.5 |
| (12) Bisethylhexyloxyphenolmethoxyphenyltriazine | 1.5 |
| (13) Hydrogen dimethicone-treated zinc oxide (average particle size: 50 nm, critical wavelength = 376 nm, absorbance at a wavelength of 370 nm = 0.628) | 8 |
| (14) Citric acid | q.s. |
| (15) Sodium citrate | q.s. |

Formulation Example 2

Milky Lotion

| (Name of component) | Content (%) |
| --- | --- |
| (1) Water | Balance |
| (2) Ethanol | 10 |
| (3) Glycerin | 3 |
| (4) Succinoglucan | 0.1 |
| (5) (Dimethylacrylamide/sodium acryloyldimethyl taurate) cross polymer | 0.3 |
| (6) Polyoxyethylene hydrogenated castor oil | 1 |
| (7) Polypropylene glycol | 1 |
| (8) Light isoparaffin | 18 |
| (9) Isostearic acid | 0.8 |
| (10) Distearyldimethylammonium chloride | 0.5 |
| (11) Octylmethoxy cinnamate | 3 |
| (12) Octocrylene | 2 |
| (13) t-Butyl methoxydibenzoylmethane | 2 |
| (14) Diethylamino hydroxybenzoyl hexyl benzoate | 2 |
| (15) Hydrogen dimethicone-treated zinc oxide (average particle size: 50 nm, critical wavelength = 376 nm, absorbance at a wavelength of 370 nm = 0.628) | 16 |
| (16) Citric acid | q.s. |
| (17) Sodium citrate | q.s. |

Formulation Example 3

Milky Lotion

| (Name of component) | Content (%) |
| --- | --- |
| (1) Water | Balance |
| (2) Ethanol | 10 |
| (3) Glycerin | 3 |
| (4) Succinoglucan | 0.1 |
| (5) (Dimethylacrylamide/sodium acryloyldimethyl taurate) cross polymer | 0.3 |
| (6) Polyoxyethylene hydrogenated castor oil | 1 |
| (7) Polypropylene glycol | 1 |
| (8) Light isoparaffin | 18 |
| (9) Isostearic acid | 0.8 |
| (10) Distearyldimethylammonium chloride | 0.5 |
| (11) Octylmethoxy cinnamate | 1.5 |
| (12) Bisethylhexyloxyphenolmethoxyphenyltriazine | 3 |
| (13) Diethylamino hydroxybenzoyl hexyl benzoate | 2 |
| (14) Hydrogen dimethicone-treated zinc oxide (average particle size: 50 nm, critical wavelength = 376 nm, absorbance at a wavelength of 370 nm = 0.628) | 20 |
| (15) Citric acid | q.s. |
| (16) Sodium citrate | q.s. |

What is claimed:

1. An oil-in-water emulsion sunscreen cosmetic composition comprising the following components (A) to (H):
    (A) a hydrophobized zinc oxide having an absorbance of 0.3 or more at a wavelength of 370 nm, wherein the hydrophobized zinc oxide has an average particle size within a range of 35 to 100 nm and wherein the hydrophobized zinc oxide is hydrophobized; by use of hydrogen dimethicone and component (A) is 8-20% by mass
    (B) a UVA absorber being solid at room temperature, and component (B) is 1.5-5% by mass;
    (C) a UVB absorber, and component (C) is 1.5-7.5% by mass;
    (D) a liquid-state higher fatty acid, and component (D) is 0.5-1.5% by mass;
    (E) a nonionic surfactant, and component (E) is 0.5-1.5% by mass;
    (F) a volatile oil, and component (F) is 10-20% by mass; and
    (G) a quaternary ammonium compound having a long-chain aliphatic group, wherein the quaternary ammonium compound having a long-chain aliphatic group is distearyldimethylammonium chloride and component (G) is 0.1-0.8% by mass; and
    (H) water.

2. The oil-in-water emulsion sunscreen cosmetic composition according to claim 1, wherein the UVA absorber is bisethylhexyloxyphenolmethoxyphenyltriazine.

3. The oil-in-water emulsion sunscreen cosmetic composition according to claim 1, wherein the UVB absorber is octylmethoxy cinnamate.

4. The oil-in-water emulsion sunscreen cosmetic composition according to claim 1, wherein the liquid-state higher fatty acid is isostearic acid.

5. The oil-in-water emulsion sunscreen cosmetic composition according to claim 1, wherein the nonionic surfactant is polyoxyethylene hydrogenated castor oil.

6. The oil-in-water emulsion sunscreen cosmetic composition according to claim 1, wherein the volatile oil is light liquid isoparaffin.

7. An oil-in-water emulsion sunscreen cosmetic composition comprising the following components (A) to (H):
(A) a hydrophobized zinc oxide having an absorbance of 0.3 or more at a wavelength of 370 nm, wherein the hydrophobized zinc oxide has an average particle size within a range of 35 to 100 nm wherein the hydrophobized zinc oxide is hydrophobized by use of hydrogen dimethicone and component (A) is 8-20% by mass
(B) a UVA absorber being solid at room temperature, and component (B) is 1.5-5% by mass;
(C) a UVB absorber, and component (C) is 1.5-7.5% by mass;
(D) a liquid-state higher fatty acid, and component (D) is 0.5-1.5% by mass;
(E) a nonionic surfactant, and component (E) is 0.5-1.5% by mass;
(F) a volatile oil, and component (F) is 10-20% by mass; and
(G) a quaternary ammonium compound having a long-chain aliphatic group wherein the quaternary ammonium compound having a long-chain aliphatic group is distearyldimethylammonium chloride and component (G) is 0.1-0.8% by mass and
(H) water;
wherein the oil-in-water emulsion sunscreen cosmetic composition has a critical wavelength ($\lambda c$) defined by the following formula:

$$\int_{290}^{\lambda c} A(\lambda)d\lambda = 0.9 \int_{290}^{400} A(\lambda)d\lambda \quad \text{[Numerical Expression 1]}$$

of 370 nm or higher.

8. The oil-in-water emulsion sunscreen cosmetic composition according to claim 7, wherein the UVA absorber is bisethylhexyloxyphenolmethoxyphenyltiazine.

9. The oil-in-water emulsion sunscreen cosmetic composition according to claim 7, wherein the UVB absorber is octylmethoxy cinnamate.

10. The oil-in-water emulsion sunscreen cosmetic composition according to claim 7, wherein the liquid-state higher fatty acid is isostearic acid.

11. The oil-in-water emulsion sunscreen cosmetic composition according to claim 7, wherein the nonionic surfactant is polyoxyethylene hydrogenated castor oil.

12. The oil-in-water emulsion sunscreen cosmetic composition according to claim 7, wherein the volatile oil is light liquid isoparaffin.

* * * * *